United States Patent [19]
Niznick

[11] Patent Number: 5,885,079
[45] Date of Patent: Mar. 23, 1999

[54] SELECTIVE SURFACE, ENDOSSEOUS DENTAL IMPLANTS

[75] Inventor: Gerald A. Niznick, Las Vegas, Nev.

[73] Assignee: Core-Vent Corporation, Calabasas Hills, Calif.

[21] Appl. No.: 102,698

[22] Filed: Jun. 22, 1998

[51] Int. Cl.⁶ .................................................. A61C 8/00
[52] U.S. Cl. ........................................................ 132/174
[58] Field of Search ............................. 433/172, 173, 433/174, 175, 176; 606/65, 66, 230, 231; 623/11, 16

[56] References Cited

U.S. PATENT DOCUMENTS

| | | | |
|---|---|---|---|
| 4,932,868 | 6/1990 | Linkow et al. | 433/174 |
| 5,078,607 | 1/1992 | Niznick . | |
| 5,174,755 | 12/1992 | Fukuda . | |
| 5,324,199 | 6/1994 | Branemark . | |
| 5,338,197 | 8/1994 | Kwan . | |
| 5,417,569 | 5/1995 | Perisse . | |
| 5,427,527 | 6/1995 | Niznick et al. | 433/174 |
| 5,571,017 | 11/1996 | Niznick | 433/174 |
| 5,639,237 | 6/1997 | Fontenot | 433/174 |
| 5,759,035 | 6/1998 | Ricci | 433/174 |
| 5,779,481 | 7/1998 | Aires | 433/174 |
| 5,795,160 | 8/1998 | Hahn et al. | 433/174 |

OTHER PUBLICATIONS

Cook S. et al.; J Oral Implant 1993: 4:288–294.
Carlsson, Albrektsson et al, JOMI 1988, vol. 3.
Buser: J. Biomet Mater Re 1991: vol. 25.
Gottlander M., Albrektsson T.: JOMI 1991: vol. 4.
Bowers, K.T. et al.: JOMI 1992:7(3), pp. 301–310.
Wennerberg, Ann, et al., Design and Surface Characteristics of 13 Commercially Available Oral IMplant Systems, JOMI, vol. 8, No. 6, pp. 622–633 (1993).
Johnson; Calif. Dental Jurnal, JOMI 1994, Special Supplement.
Buser JOMI 1991, vol. 4.
Schupback P. et al.: Clin Oral Impl. res. 1994 5:55–65.
Schliephake 1993, JOMI vol. 8.

Primary Examiner—Gene Mancene
Assistant Examiner—Pedro Philogene
Attorney, Agent, or Firm—Patrick F. Bright

[57] ABSTRACT

Endosseous dental implants having generally cylindrical-shaped or tapering bodies and, in some cases, external threads or ribs over a substantial portion of their external surface, may include internal or external wrench-engaging surfaces at the proximal end portion and include, below a relatively smooth proximal end or neck portion, an external transition zone with a rougher surface, and a body portion having greater surface roughness than the transition zone, or, on the body portion, an HA or TPS coating, to promote attachment of the implant to bone tissue when the implant is placed in a passage formed in bone tissue to receive the implant.

33 Claims, 3 Drawing Sheets

SELECTIVE SURFACE, ENDOSSEOUS DENTAL IMPLANTS

BACKGROUND OF THE INVENTION

Implants with threads over a substantial portion of their external surface, whether for self-tapping insertion or otherwise, implants that are externally unthreaded and implants that are both externally ribbed and externally threaded, are generally known and commercially available. Externally-threaded implants usually have an unthreaded portion at the proximal end of the implant that is commonly referred to as the neck portion, with the remainder of the external surface substantially threaded to or near to the distal end of the implant. Where present, self-tapping features serve the function of cutting threads in a cylindrical passage formed in the jawbone tissue of a person to receive the implant as the externally-threaded implant is rotated to a depth that places the neck of the implant above, at or just below the crest of the jawbone.

Self-tapping insertion of an externally-threaded implant is accomplished by forming, as by machining, one or more grooves on the sidewall extending upwardly from the distal end parallel to the longitudinal axis of the dental implant and through at least one full diameter external thread. These grooves create cutting edges that function to scrape off bone chips during threading of the implant into the cylindrical hole prepared in the bone tissue. The grooves also provide cavities with adequate volume to contain the bone tissue material to allow full seating of the implant.

Some self-tapping implants also provide a through-hole connecting two channels on opposite sides of the implant to provide additional cavity space to harbor bone chips and to further stabilize the implant once bone regeneration has occurred.

Self-tapping insertion of the implant has proven advantageous from a time-saving standpoint (Fribert B. et al.; JOMI 1992; 1:80–84) by reducing surgical time by 3 minutes or more per implant. Self-tapping insertion of the externally-threaded implants also improves the initial stability needed for direct bone attachment following a healing period, referred to as osseointegration, by creating a more intimate contact with the bone than placement following use of a bone tap surgical instrument. This more intimate initial fit has also been demonstrated to result in an increased percentage of bone attachment to the implant surface after healing (Cook S. et al. J Oral Implant 1993: 4:288–294). For self-tapping insertion to be effective in dense bone, the cutting edges created by the grooves through the distal threads must be sharp enough to shave bone chips. Roughening the implant surface by grit-blasting, or by grit-blasting followed by acid etching, or by grit blasting followed by coating the surface of the implant with Titanium Plasma Spray (TPS) or with a bio-reactive material such as Hydroxylapatite (HA), rounds these cutting edges, decreasing the cutting efficiency of the self-tapping features. This can necessitate increasing the torque forces needed to insert the self-tapping implant in dense bone to the point that damage may occur to the wrench-engaging feature in the proximal portion of the implant, resulting in failure to seat the implant fully in the bone chamber.

Self-tapping screw implants are usually machined from a biocompatible metal of suitable strength such as commercially-pure titanium or from medical grade titanium alloy. The selection of Grade 1 or 2 commercially-pure (CP) titanium, with tensile strengths lower than Grade 3 or 4 CP titanium or titanium alloy (6Al/4V), may preclude the incorporation of through-holes because of the lower tensile strength. Such lower tensile strength may also limit the density of bone that the implant can self-tap into because of the lower resistance to distortion of the wrench-engaging surfaces at or near the proximal end of the implant as higher torque forces are required to cut through dense bone.

Some self-tapping screw implants are sold with a machined surface (Nobelpharma, Inc. implants and others (Core-Vent Corporation's SCREW-VENT implant) are further treated after machining by washing in dilute HF acid to remove loose titanium particles and other contaminants. Acid etching creates pits on the surface of the implant, similar in surface roughness to the untreated machined surface. Machined and etched surfaces are relatively smooth compared to grit blasted, TPS-coated or HA coated surfaces.

Some commercially available self-tapping screw implants have their threaded external surfaces treated to increase surface roughness while maintaining the neck portion relatively smooth by leaving it with a machined or etched surface or by mechanically polishing the surface. A smooth neck portion promotes mucosal tissue health if it becomes exposed to the mucosa. The texture of the implant's external surface is increased in roughness by grit-blasting with a variety of bio-compatible particles such as titanium oxide (Astra implants), aluminum oxide (CORE-VENT implant, pre-1986) or tri-calcium phosphate (Screw-Vent, post 1997). The degree of roughness can be varied by varying the size and hardness of the abrasive particles, and by varying the force and duration of the blasting procedure. Some screw implants, after machining, are grit-blasted to roughen the surface preparatory to applying a coating of either Titanium Plasma Spray, (as in the Bio-Vent, Friatec, Straumann ITI implants), which provides both a rough and porous surface, or a coating of a bio-active material such as Hydroxylapatite (HA: STERI-OSS, SCREW-VENT and MICRO-VENT implants). HA may be densely applied and of high crystallinity, which produces a surface roughness approximating that of a small-particle grit blasted surface, or may be less dense and/or less crystalline, which produces a surface roughness that could match or exceed that of TPS coating or large particle grit-blasting.

Surface Texture and Material Effect Bone Attachment

Studies have documented increased removal torques with implants having increased surface roughness (Carlisson, Albrektsson et al., JOMI 1988: Vol. 3), and other studies have shown increased bone attachment to rougher surfaces (Buser: J Biomet Mater Re 1991: Vol. 25). A study comparing bone attachment to HA coated and machined surfaces demonstrated a faster, more complete attachment to the HA surface in the critical, early healing period (Gottlander M., Albrektsson T.: JOMI 1991: Vol. 4).

At the cellular level, one study (Bowers, K. T. et al.: JOMI 1992:7(3) p. 301–310) found higher levels of attachment of osteoblast-like cells to surfaces with random roughness created by grit-blasting and acid etching compared to parallel grooved surfaces similar in appearance to a machined surface, created in this study by grinding the surface with 120 and 60 gauge grit. This was true despite the fact that the surface roughness of the grooved surface, created by grit polishing, was rougher than that produced by the acid etch procedure, indicating that random roughness promotes bone attachment better than parallel or concentric grooves.

Another study comparing bone attachment strength to HA and to a rougher grit-blasted surface documented 77% increase in torsional strength for the HA coated surface, indicating that HA is bio-active and created a chemical as well as mechanical bond with the bone.

Studies have measured the differences in surface roughness of commercially-available implants using scanning microscope profilometry [Wennerberg, Ann. et al.,*Design and Surface Characteristics of 13 Commercially Available Oral Implant Systems*, JOMI, Vol. 8, No. 6, pages 622–633 (1993)], and determined that the machined Branemark surface was the smoothest with an average difference, called $R_t$, of about 10 microns between the peaks and valleys of the surface texture. The Wennerberg article defines the term $R_t$, at page 623, to mean the maximum peak-to-valley height of the profile of the implant surface and the assessment length, measured in micrometers. The assessment length is the length of the implant subjected to analysis.

Using the $R_t$ measurement standard as set forth in the Wennerberg article, the acid etched surface of a SCREW-VENT implant, made from commercially-pure titanium, measured an average of about 10 microns. The grit-blasted and acid-etched surface of the titanium alloy Core-Vent has an average $R_t$ value of about 18 microns. The TPS coated surface of the IMZ implant had an $R_t$ value of about 25 microns. HA coated surfaces of four implants were measured in the Wennerberg study, which reported an $R_t$ value of about 18 microns for Calcitek's highly dense, crystalline HA surface. Several other HA coatings, which are more porous and less crystalline, had $R_t$ values up to about 40 microns.

Regardless of the smoothness of the HA surface, it is unsuitable material for coating the neck portion of an implant that may become exposed to oral mucosa when crestal bone recession occurs around the top of the implant. Coated surfaces so exposed to the oral environment either increase the attachment of dental plaque, or dissolve, exposing the rough, grit-blasted undersurface, which also increases the attachment of dental plaque. Plaque around the exposed neck of an implant causes adverse mucosal tissue reactions and ultimately increased bone loss, just as with natural teeth. Crestal bone cratering and associated soft tissue complications have been reported with Calcitek's non-threaded cylinder implants that have a dense, relatively smooth, HA coating all the way to the top of the implant (Johnson; Calif. Dental Journal, JOMI 1994, Special Supplement).

Exposure of the machined surface of the neck of the implant above the crest of the bone routinely occurs with the Branemark machined implants, but long-term studies do not indicate that such exposure of the machined surface to mucosal tissue attracts dental plaque any more than with natural teeth. Oral hygiene can be maintained on this relatively smooth surface, minimizing soft tissue complications. A VA multicenter study reported an average of 0.75 to 1.5 mm of bone loss 6 months after exposure for both acid etched (smooth) and for HA-coated implants with a 0.5 mm acid-etched neck, exposing HA coating to mucosal tissue.

The clinical complications of exposure of the rough TPS coating into the gingival area have been documented in a clinical study of 54 ITI implants where all the implants osseointegrated. However, within 3 years, 3 implants exhibited recurrent per-implant infections and were classified as late failures (Buser JOMI 1991, Vol. 4).

Implant manufacturers, recognizing the potential benefits of the bio-active HA coatings and the rougher surfaces of the TPS coatings or large particle grit blasting with or without subsequent acid etching, have attempted to limit the complications associated with exposure to these rough or bio-reactive surfaces to the oral cavity by maintaining an uncoated machined (3i), or acid etched (Core-Vent) metal portion extending down from the top of the TPS or HA coated implant a distance ranging from 0.5 mm to over 3 mm in length. The longer the smooth neck, the more extensive the bone loss, but the shorter the smooth neck, the more likely the exposure of mucosal tissue to the roughened or coated external implant surface.

SUMMARY OF THE INVENTION

This invention relates to externally-unthreaded, externally-threaded and/or externally-ribbed, endosseous dental implants. More particularly, this invention relates to such endosseous dental implants with generally cylindrical-shaped or tapering bodies. These implants preferably include self-tapping threads at or near their distal end. Where self-tapping, these screw implants improve initial stability in bone, thereby reducing early failures and reduce surgical time for implantation. Preferably, these implants include internal or external wrench-engaging surfaces at or near the proximal end of the implants, and an internal passage extending into the body of the implants from an opening at the proximal end of the implants that receives and engages a separate, secondary part, sometimes called an abutment or an adaptor. Alternatively, the implants may only have threaded internal shafts and no wrench-engaging surfaces. Alternatively, these implants may be one-part implants that do not require a separate, secondary part.

The endosseous dental implants of this invention have generally cylindrical-shaped bodies, or bodies that taper in steps or otherwise to a smaller diameter towards the distal end, with or without external threads over a substantial portion of their external surface. In some embodiments, the distal end also includes a longitudinal groove on the sidewall extending through the external threads and extending upwardly from the distal end of the dental implant parallel to the longitudinal axis of the dental implant itself. In some embodiments, these implants include one or more through-holes near the distal end perpendicular to the longitudinal axis of the dental implant. In some of these embodiments, the through-hole communicates with the distal end of the implant via a vertical through-hole extending into the body of the implant from the distal end of the implant to the through-hole.

In preferred embodiments up to four specific areas of the external surface of the screw implant can be distinguished by surface roughness or surface coating material to improve clinical success. The neck is preferably at least partially annular, unthreaded, uncoated and relatively smooth to allow maintenance of oral hygiene, as where the neck is exposed to an oral environment. The neck surface may be machined, as in the Branemark/Nobel-pharma dental implant, or machined and acid etched to remove loose titanium particles from the surface, as in Core-Vent Corporation's Screw-Vent implant, or the neck may be polished or made of a ceramic. If polished or made of ceramic, the neck preferably has a roughness equal to or less than the roughness of such machined or machined/acid-etched necks, as described more particularly in the Wennerberg article. Acid etched surfaces have been shown in studies to provide an acceptable surface for attachment of both mucosal and bone tissue (Schupback P. et al.: Clin Oral Impl. res. 1994 5:55–65). Alternatively, the neck may be coated with ceramic to form a smooth external surface.

In preferred embodiments, the neck portion of the implant is sufficiently smooth to minimize adherence of dental plaque that can cause an adverse mucosal tissue reaction if exposed to an oral environment as a result of crestal bone loss or otherwise. An average $R_t$ value of about 15 microns or less for the neck portion is preferred.

Between the neck portion and the body portion of the implant is a transition zone, preferably having a length of about 1 to about 2 millimeters. This transition zone is about 50% rougher than the neck portion, and is sufficiently rough to minimize resorption of bone tissue surrounding the transition zone, thus minimizing exposure of the even rougher coated body portion to the oral cavity. In preferred embodiments, this roughened transition zone is created by grit-blasting with a resorbable medium or abrasive such as tri-calcium phosphate, or by using metal oxide particles of appropriate size and under appropriate conditions with or without a subsequent acid wash. Preferably, the $R_t$ value of this surface is in the range of about 15 to about 20 microns.

The threaded distal end of the implant is preferably uncoated, and has a machined or acid-etched surface, and more preferably has a sufficiently smooth surface to maintain sharp cutting threads for self-tapping insertion, thereby shortening surgical time and improving initial stability. Alternatively, the distal end of the implant may be wholly or partially roughened, or HA coated or TPS coated.

The body portion of the implant, contiguous with and between the distal end and the transition zone, is roughened, or coated with a bio-active material such as HA, or both, to increase the percentage of the external surface in contact with bone, thus enabling the implant to better withstand biting forces. If uncoated, this body portion is at least about 50% rougher than the transition zone, and at least about 100% rougher than the external surface of the relatively smooth neck portion of the implant. If coated, the body portion is preferably HA coated or TPS coated, most preferably over more than about 90% of its area. Preferably, the $R_t$ value for this body portion, if roughened by blasting or TPS coating, is at least about 25 microns.

In some embodiments, an HA coating on the body portion of the implant has a high crystallinity which reduces solubility, but maintains bio-active benefits that encourage stronger, more rapid bone attachment. Such high crystalline HA may have an $R_t$ value approximating 20 microns.

Preferably, the distal portion of the implant has a relatively smooth, machined or etched surface with an $R_t$ value of about 10 microns or less. In contrast, the adjacent surface of the body of the implant above the distal portion, if uncoated, has an $R_t$ value at least as twice as great as the machined or acid etched distal portion. Alternatively, the distal end may have a roughness similar to the roughness of the transition zone, with the body portion being 50% rougher than the transition zone.

In preferred embodiments, the distal portion has an acid-etched surface. Such a surface results from acid etching with a concentration of HF or other suitable acid capable of controlled removal of approximately 0.001 inch of the surface when used in the appropriate concentration and for the appropriate time to create the desired relatively smooth surface texture, and to remove loose particles, if any, formed on the implant surface during machining. One study showed that these particles, if unremoved from the implant become embedded in the walls of the cylindrical bone socket during self-tapping insertion of the threaded implant (Schliephake 1993, JOMI Vol. 8).

In preferred embodiments, one or more longitudinal grooves on the sidewalls extend through the external threads in the distal portion, upwardly from or near the distal end of the dental implant parallel to the longitudinal axis of the dental implant itself, creating relatively sharp edges and relief areas for cutting and harvesting bone chips during self-tapping insertion in dense bone. In some embodiments, the distal portion also includes one or more through-holes. Some of these embodiments also include a cavity inside the implant near the distal end as additional space for bone chips and to increase stabilization of the implant after healing and bone regeneration has occurred.

The proximal end of these dental implants preferably includes either internal, wrench-engaging surfaces or external, wrench-engaging surfaces. Preferably, these wrench-engaging surfaces are multi-sided and more preferably have four to eight sides and, if external, are formed on the surface at the top of the implant, as in Core-Vent Corporation's SWEDE-VENT® implant. If internal, the multi-sided surfaces lie just below the upper surface of the implant inside an internal passage, as in Core-Vent Corporation's SCREW-VENT® implant.

In some embodiments, whether the implants have external or internal wrench-engaging surfaces, the implants also include an internal passage for receiving and engaging a secondary implant part, sometimes called a post, adapter or abutment. Where the internal passage is threaded, at least in part, the abutment can be externally threaded to engage the internal threads inside this passage, or the abutment can be cementable inside this internal passage. Suitable abutments may be one-piece, two-piece or three-piece and, if multi-part, may include a portion that interfits frictionally with internal (e.g. Core-Vent Corporation's SCREW-VENT implants) or external (e.g. Core-Vent Corporation's SWEDE-VENT® TL dental implants) wrench-engaging surfaces to minimize rotation of the abutment in relation to the implant itself.

BRIEF DESCRIPTION OF THE DRAWINGS

The multi-surfaced implants of this invention can better be understood by reference to the drawings, in which:

The implants of FIGS. 1A/1B, 2A/2B, 3A/3B, 4A/4B and 5A/5B have an internally threaded passage to engage externally-threaded abutments. FIGS. 1A/1B and 4A/4B show an external, wrench-engaging, multi-sided surface for engaging a tool to place the implant into a generally cylindrical passage formed in a person's jawbone to receive the implant. The implants of FIGS. 2A/2B and 3A/3B have wrench-engaging, multi-sided surfaces just below the top surface of the implant and within the internal passage inside the implant.

DETAILED DESCRIPTION OF THE PREFERRED EMBODIMENTS

Figure 1A:
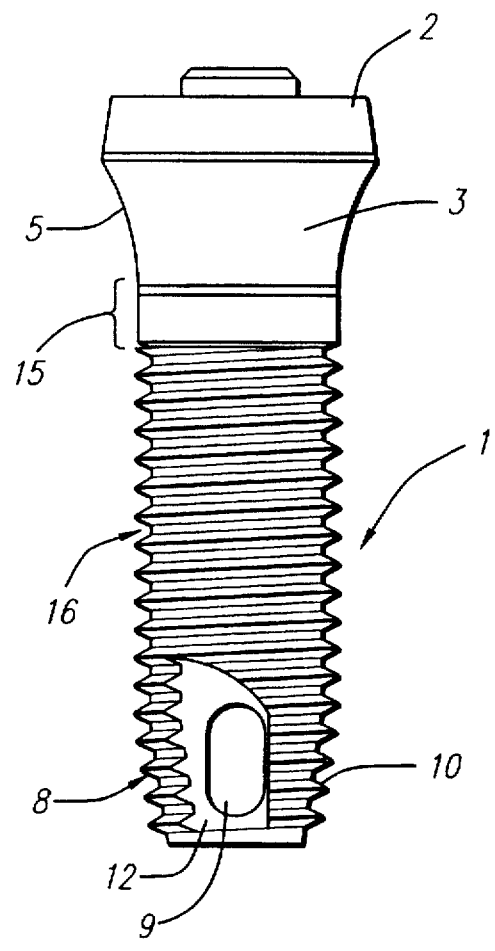
FIGS. 1A and 1B show a self-tapping, generally cylindrical, one-piece endosseous dental implant having a smooth proximal end or neck, a roughened transition zone on its external threaded body surface, and a body portion on its external threaded surface that is rougher than the neck and the transition zone.
Figure 1B:
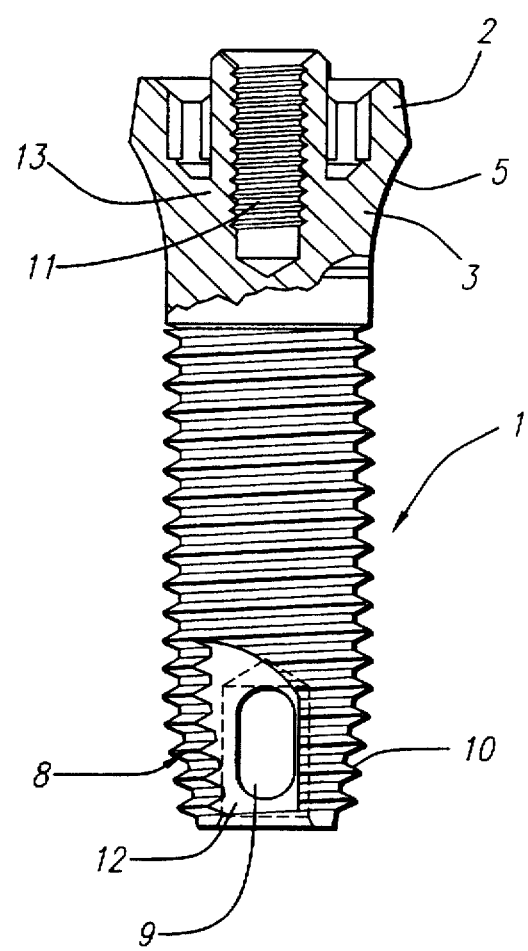

FIGS. 1A and 1B show endosseous, externally threaded, dental implant 1 having a generally cylindrical external shape. At distal end 10 of implant 1 are uncoated, self-tapping threads 8, through-hole 9, and internal cavity 12 that receives bone chips and fluid formed as implant 1 is inserted into a generally cylindrical passage formed in the jawbone of a patient to receive implant 1. At the proximal end 5 of implant 1 is uncoated, unthreaded, relatively smooth neck portion 3. Atop neck portion 3 is multi-sided, external wrench-engaging surface 2. Inside implant 1 and extending downwardly and inwardly from proximal end 5 is internal passage 13. Proximal end 5 has an $R_r$ average value of less than about 10 microns. Internal passage 13 has an internally-threaded region 11 that can engage a complementary, threaded adapter or post.

The transition zone 15 is relatively rough, with $R_r$ value of about 10–20 microns or greater, or at least about 50% greater than the roughness of the uncoated proximal end surfaces 3. Transition zone 15 is blasted over about 90% or more of its surface, preferably with a resorbable medium such as tri-calcium phosphate.

Body portion 16 is coated with HA or TPS or may be grit blasted to be rougher than transition zone 15, with an average $R_r$ value of about 25 microns or greater, or at least about 100% greater than the roughness of proximal end surface 3. HA coating or TPS coating, or alternatively grit blasting, can be used to form the relatively rough surface of body portion 16. Distal end portion 10 may be coated or uncoated, and may include self-tapping threads, if desired, and need not be roughened, but may be as smooth or smoother than proximal end 3, or as rough as the transition zone.

Figure 2A:
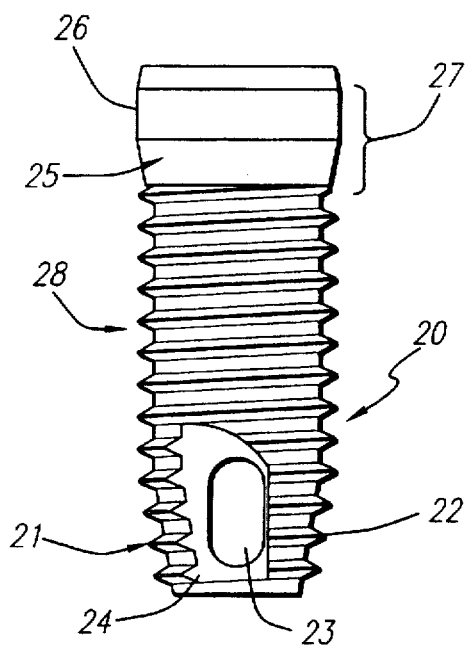
FIGS. 2A and 2B show another generally cylindrical, endosseous dental implant having a smooth proximal end or neck, a transition zone that is rougher than the neck, and a body portion that is rougher than the neck and the transition zone, except for a smoother (preferably self-tapping) threaded distal end portion.
Figure 2B:
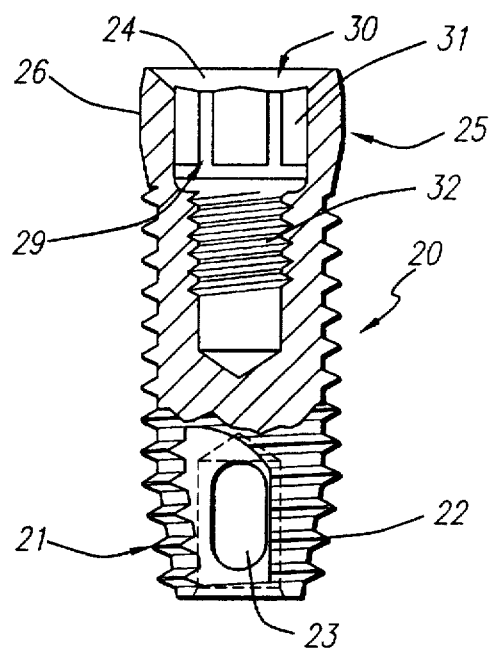

FIGS. 2A and 2B show generally cylindrical, endosseous dental implant 20 having a generally cylindrical shape including relatively smooth distal end 22 that includes self-tapping threads 21. Distal end portion 22 could be unthreaded, and either uncoated, roughened or coated, as described. Above distal end 22 is through-hole 23 and internal cavity 24 that receives blood, bone chips and other debris formed as implant 20 is screwed into a generally cylindrical passage formed in the jawbone of a person to receive implant 20. Implant 20 also includes, at its proximal end 25, relatively smooth annular surface 26 above roughened transition zone 27 and body portion 28, respectively.

Inside implant 20 is internal passage 29 that includes, just below proximal opening 30, an annular-shape, chamfered region 29. Below chamfered region 29 is multi-sided, wrench-engaging surface 31, and, below surface 31, internally threaded passage 32. The internal threads in passage 32 are formed and shaped to engage a threaded adapter or abutment or, alternatively, a cementable adapter.

Implant 20 includes external, transition zone 27 that is relatively rough, with an average $R_r$ value of about 20 microns or more, or at least about 50% rougher than the uncoated, relatively smooth proximal end 26. Blasting, preferably with a resorbable medium such as tri-calcium phosphate, can be used to form surface 27.

Implant 20 also includes body portion 28 with a surface that is rougher than surface 27 and rougher than neck portion 26. Preferably, the average $R_r$ value of the surface texture 28 is about 25 microns or greater, or at least 100% greater than the roughness of the uncoated, relatively smooth proximal end 26. Alternatively, smooth highly crystalline or rough amorphous HA coating with varying surface roughness or TPS coating, or grit blasting can be used to form surface 28.

Figure 3A:
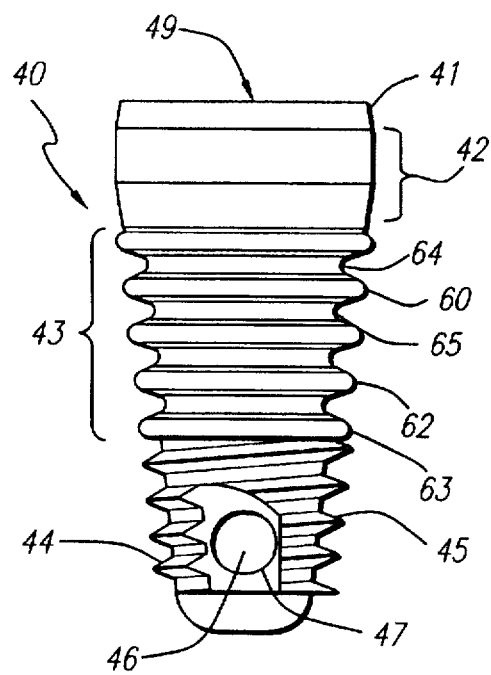
FIGS. 3A and 3B show another generally cylindrical, tapering endosseous dental implant having a smooth proximal end or neck, a transition zone that is at least about 50% rougher than the neck portion, and a body portion that is at least about 100% rougher than the neck portion, except for a threaded, smoother distal end portion. The transition zone and body portion include a plurality of parallel ribs on the external surface of the implant.
Figure 3B:
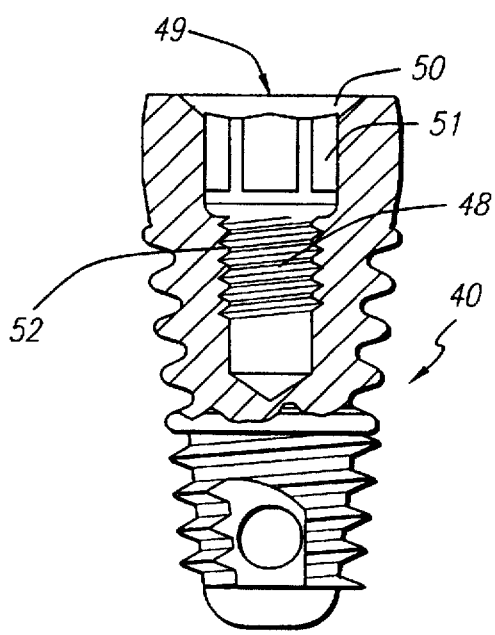

FIGS. 3A and 3B show endosseous, tapering dental implant 40 that includes smooth neck portion 41, transition zone 42, body 43 and threaded distal end portion 44. Distal portion 44 includes self-tapping threads 45, through-hole 46 and internal cavity 47 that receives blood, bone chips and other debris formed as implant 40 is screwed into a generally cylindrical passage formed in the jawbone of a person to receive the implant 40.

Inside implant 40 is internal passage 48 that includes, just below proximal opening 49, an annular-shaped chamfered region 50. Below chamfered region 50 is multi-sided, wrench-engaging surface 51, and, below surface 51, internal threaded passage 52. The internal threads in passage 52 are formed and shaped to engage a threaded adapter or abutment or, alternatively, a cementable adapter.

Implant 40 has an external transition zone 42 with a surface that is rougher than neck portion 41. Transition zone 42 has an average $R_r$ value of at least about 20 microns or more, or at least about 50% greater than the average $R_r$ value of the uncoated neck portion 41.

Body portion 43 is rougher than transition zone 42 and rougher than neck portion 41. Preferably, body portion 43 has an average $R_r$ value of about 25 microns or more, or at least about 100% greater than the roughness of neck portion 41, but in the case of highly crystalline HA may be less than 25 microns.

HA coating, TPS coating or, alternatively grit blasting, can be used to form body portion 43. Portion 43 could alternatively be unthreaded and either roughened or coated. As shown in FIG. 3, body 43 includes a series of concentric parallel ribs 60, 61, 62 and 63, separated from one another by grooves such as grooves 64 and 65.

Figure 4A:
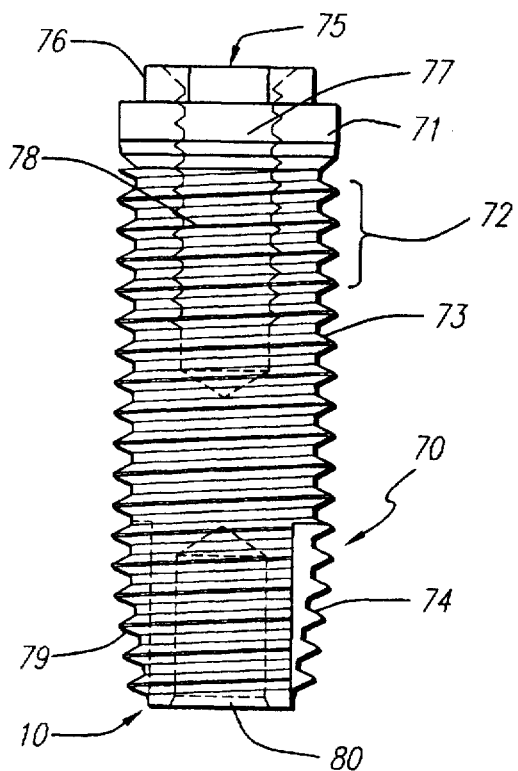
FIGS. 4A and 4B show another generally cylindrical, endosseous dental implant having a smooth proximal end or neck, a transition zone that is rougher than the neck, and a body portion that is rougher than the neck and transition zone.
Figure 4B:
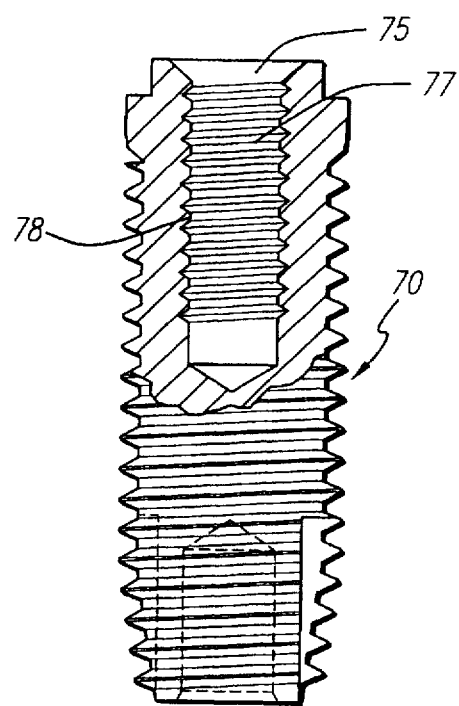

FIGS. 4A and 4B show another generally cylindrical, endosseous dental implant 70 that includes smooth neck portion 71, transition zone 72, body 43 and threaded distal end portion 74. Distal portion 74b includes self-tapping threads 79 and internal cavity 80 that receive blood, bone chips and other debris formed as implant 70 is screwed into a generally cylindrical passaged formed in a jawbone of a person to receive implant 70.

Atop implant 70 is external, multi-sided, wrench-engaging projection 76 that includes a proximal opening 75 into internal passage 77 with its internal threads 78. The internal threads in passage 77 are formed and shaped to engage a threaded adapter or abutment or, alternatively, a cementable adapter.

Implant 70 has an external transition zone 72 with a surface that is rougher than the neck portion 71. Transition zone 72 has an average $R_r$ value of at least about 25 microns or more, or at least about 50% greater than the average $R_r$ value of the neck portion 71.

Body portion 73 is rougher than transition zone 72 and rougher than neck portion 71. Preferably, body portion 73 has an average $R_r$ value of about 25 microns or more, or at least about 100% greater than the roughness of neck portion 71.

HA coating, TPS coating, or alternatively, grit blasting, can be used to form the surface of body portion 43. Instead of, or in addition to being roughened, body portion 43 can simply be coated with HA coating or TPS coating, in contrast to uncoated neck portion 71. Body portion 73 could alternatively be unthreaded, but would still be either roughened, or TPS or HA coated.

Figure 5A:
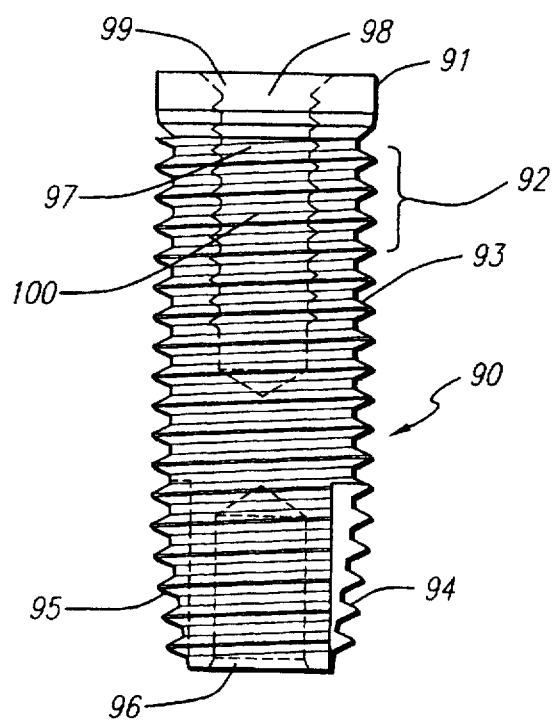
FIGS. 5A and 5B show another generally cylindrical, endosseous dental implant having a smooth proximal end or neck, a transition zone that is rougher than the neck, and a body portion that is rougher than the neck and transition zone.
Figure 5B:
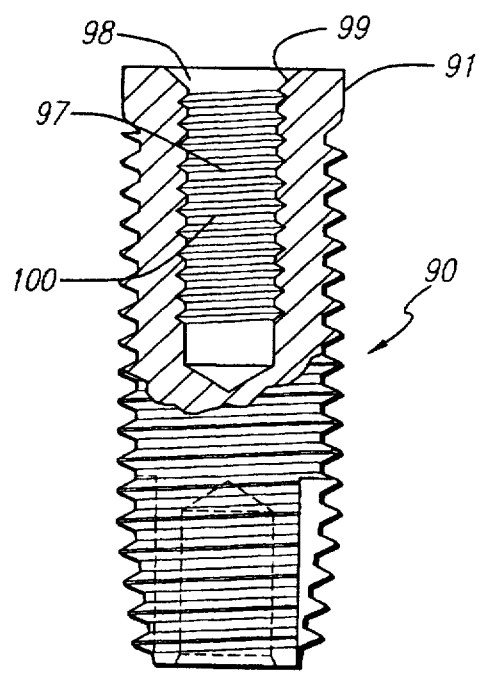

FIGS. 5A and 5B show endosseous, generally cylindrical dental implant 90 that includes smooth neck portion 91, transition zone 92, body portion 93 and threaded distal end portion 94. Distal portion 94 includes self-tapping threads 95, and internal cavity 96 that receives blood, bone chips and other debris formed as implant 90 is screwed into a generally cylindrical passage formed in the jawbone of a person to receive implant 90.

Inside implant 90 is internal passage 97 that includes, just below proximal opening 98, an annular shaped chamfered region 99. Below chamfered region 99 is internally threaded passage 97. The internal threads 100 in passage 97 are formed and shaped to engage a threaded adapter, threaded abutment or cementable adapter or abutment.

Implant 90 has an external transition zone 91 with a surface that is rougher than neck portion 91. Transition zone 92 has an average $R_t$ value that is at least about 20 microns or more, or at least about 50% greater than the average $R_t$ value of the uncoated neck portion 91.

Body portion 93 is rougher than transition zone 92 and is rougher than neck portion 91. Preferably, body portion 93 has an average $R_t$ about 25 microns or more, or at least about 100% greater than the roughness of neck portion 91.

HA coating, TPS coating, or alternatively, grist blasting, can be used to form the surface of body portion 93. Body portion 93 could alternatively be unthreaded, and either roughened or coated.

A study entitled "Optimization Of Surface Micromorphology For Enhanced Osteoblast Responses In Vitro" by K. Bowers et al., published in the *Journal of Maxillofacial Implants*, 1992, Vol. 3, pp. 302–310, suggested that bone cell attachment to dental implant surfaces improves if the surface roughness of the implant that contacts bone tissue has randomized roughness. Preferred embodiments of the implants of this invention therefore include relatively rough, external upper and lower mid-portions with random roughness.

What is claimed is:

1. An endosseous dental implant having a shape selected from the group consisting of generally cylindrical and generally tapering and including, at its distal end, self-tapping threads, and near its proximal end, an internally threaded shaft, said distal end and said proximal end having an average $R_t$ value of up to about 10 microns, and, between said distal and proximal ends, a transition zone contiguous to said proximal end having an average $R_t$ value of about 15 to about 20 microns, and, between said transition zone and said distal end, a body portion that is selected from the group consisting of uncoated, HA coated, and TPS coated, and where uncoated, has an average $R_t$ value of at least about 25 microns.

2. The dental implant of claim 1 wherein the distal end of said implant includes at least one through-hole and at least one internal cavity of sufficient size and shape to receive and hold solids and liquids formed by the self-cutting threads as the implant is inserted into said passage.

3. The implant of claim 1 wherein said body portion is HA coated.

4. The implant of claim 1 wherein said body portion is coated with titanium plasma spray.

5. The implant of claim 1 wherein said body portion is formed by grit-blasting or by grit-blasting followed by acid etching.

6. The endosseous dental implant of claim 1 or claim 2 or claim 4 or claim 5 wherein wrench-engaging surfaces are at the top surface of said implant and project upwardly from said top surface.

7. The endosseous dental implant of claim 1 or claim 2 or claim 4 or claim 5 wherein wrench-engaging surfaces are inside said implant, below the top surface of said implant, and within the external walls of said implant.

8. An endosseous dental implant having a shape selected from the group consisting of generally cylindrical and generally tapering including a relatively smooth proximal end, an internally-threaded shaft, a body portion that is selected from the group consisting of uncoated, HA coated, and TPS coated, and where uncoated, has an average $R_t$ value at least about 100% greater than said proximal end, and, between said distal end and said proximal end, a transition zone having an average $R_t$ value at least about 50% greater than the average $R_t$ value of said proximal end.

9. The dental implant of claim 8 wherein the distal end of said implant includes at least one through-hole and at least one internal cavity of sufficient size and shape to receive and hold solids and liquids formed by the self-cutting threads as the implant is inserted into said passage.

10. The implant of claim 8 wherein said body portion is HA coated.

11. The implant of claim 8 wherein said body portion is coated with titanium plasma spray.

12. The implant of claim 8 wherein said body portion is formed by grit-blasting, or by grit-blasting followed by acid etching.

13. The endosseous dental implant of claim 8 or claim 9 or claim 10 or claim 11 or claim 12 wherein said distal end and said proximal end have an average $R_t$ value of up to about 10 microns.

14. The endosseous dental implant of claim 8 or claim 9 or claim 10 or claim 11 or claim 12 wherein said wrench-engaging surfaces are at the top surface of said implant and project upwardly from said top surface.

15. The dental implant of claim 1 or claim 2 or claim 3 or claim 4 or claim 5 or claim 6 or claim 7 or claim 8 or claim 9 or claim 10 or claim 11 or claim 12 or claim 13 or claim 14 wherein said transition zone and said body portion are externally-threaded.

16. An endosseous dental implant having a shape selected from the group consisting of generally cylindrical and generally tapering and including, at its proximal end, an external surface having an average $R_t$ value of up to about 10 microns, and, contiguous to said proximal end, a transition zone having an average $R_t$ value of about 15 to about 20 microns, and, contiguous to said transition zone, a body portion that is selected from the group consisting of uncoated, HA coated, and TPS coated, and where uncoated has an average $R_t$ value of at least about 25 microns.

17. The dental implant of claim 16 wherein the distal end of the implant includes at least one through-hole and at least one internal cavity of sufficient size and shape to receive and hold solids and liquids formed by the self-cutting threads as the implant is inserted into said passage.

18. The implant of claim 16 wherein said body portion is HA coated.

19. The implant of claim 16 wherein said body portion is coated with titanium plasma spray.

20. The implant of claim 16 wherein said body portion is formed by grit-blasting or by grit blasting followed by acid etching.

21. The endosseous dental implant of claim 16 or claim 17 or claim 18 or claim 19 or claim 20 wherein said distal end portion and said proximal end portion each has an average $R_t$ value of up to about 10 microns.

22. The endosseous dental implant of claim 16 or claim 17 or claim 18 or claim 19 or claim 20 wherein said transition zone and said body are externally threaded.

23. The endosseous dental implant of claim 16 or claim 17 or claim 18 or claim 19 or claim 20 wherein said distal end portion and said transition zone each has an average $R_t$ value of up to about 20 microns.

24. An endosseous dental implant having a shape selected from the group consisting of generally cylindrical and generally tapering and including, at its proximal end, an external surface and contiguous with and below said proximal end, a transition zone having an average $R_t$ value that is at least about 50% greater than the average $R_t$ of said proximal end, and, contiguous with and below said transition zone, a body portion that is selected from the group consisting of uncoated, HA coated, and TPS coated, and where uncoated has an average $R_t$ value of at least about 100% greater than the roughness of said proximal end, said body portion including a distal end portion that has an average $R_t$ value similar to the $R_t$ value of at least one member selected from the group consisting of said proximal end, said transition zone, and said body portion.

25. The dental implant of claim 24 wherein the distal end of the implant includes at least one through-hole and at least one internal cavity of sufficient size and shape to receive and hold solids and liquids formed by the self-cutting threads as the implant is inserted into said passage.

26. The implant of claim 24 wherein said body portion is HA coated.

27. The implant of claim 24 wherein said body portion is coated with titanium plasma spray.

28. The implant of claim 24 wherein said body portion is formed by grit-blasting or by grit-blasting followed by acid etching.

29. An endosseous dental implant having a shape selected from the group consisting of generally cylindrical and generally tapering and including, at its proximal end, an external surface that is selected from the group consisting of machined, polished, made of a ceramic, and acid etched, and, contiguous with and below said proximal end, a transition zone having an average roughness that is at least about 50% greater than the average roughness of said proximal end, and, contiguous with and below said transition zone, a body portion that is selected from the group consisting of uncoated HA coated, and TPS coated, and where uncoated has an average roughness of at least about 100% greater than the roughness of said proximal end, said body portion including a distal end portion that has an average roughness similar to a member selected from the group consisting of said proximal end, said transition zone, and said body portion.

30. The dental implant of claim 29 wherein the distal end of said implant includes at least one through-hole.

31. The dental implant of claim 29 wherein said body portion is HA coated.

32. The dental implant of claim 29 wherein said body portion is coated with titanium plasma spray.

33. The implant of claim 29 wherein said body portion is formed by a member selected from the group consisting of grit-blasting, and grit-blasting followed by acid etching.

* * * * *